United States Patent
Takemura et al.

(10) Patent No.: US 6,194,434 B1
(45) Date of Patent: Feb. 27, 2001

(54) CYCLOALKYLAMINOMETHYLPYRROLIDINE DERIVATIVES

(75) Inventors: Makoto Takemura; Youichi Kimura; Katsuhiro Kawakami; Hitoshi Ohki, all of Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/171,637

(22) PCT Filed: Apr. 24, 1997

(86) PCT No.: PCT/JP97/01446

§ 371 Date: Oct. 22, 1998

§ 102(e) Date: Oct. 22, 1998

(87) PCT Pub. No.: WO97/40037

PCT Pub. Date: Oct. 30, 1997

(30) Foreign Application Priority Data

Mar. 24, 1996 (JP) .................................................. 8-102334

(51) Int. Cl.[7] .......................... A61K 31/47; C07D 215/16; C07D 215/20
(52) U.S. Cl. ............................................ 514/312; 546/156
(58) Field of Search .............................. 514/312; 546/156

(56) References Cited

U.S. PATENT DOCUMENTS

| 4,657,913 | * | 4/1987 | Mich | 514/278 |
|---|---|---|---|---|
| 4,771,055 | * | 9/1988 | Domagala | 514/312 |
| 4,780,468 | * | 10/1988 | Bridges | 514/312 |
| 4,954,507 | * | 9/1990 | weber | 514/300 |
| 4,965,273 | * | 10/1990 | Weber | 514/300 |
| 5,173,484 | * | 12/1992 | Petersen . | |
| 5,284,842 | * | 2/1994 | Petersen . | |
| 5,453,422 | * | 9/1995 | Petersen . | |

FOREIGN PATENT DOCUMENTS

| 0 106 489 | 4/1984 | (EP) . | |
|---|---|---|---|
| 0 202 763 | 11/1986 | (EP) . | |
| 0 255 908 | 2/1988 | (EP) . | |
| 0 302 525 | 2/1989 | (EP) . | |
| 0 326 916 | 8/1989 | (EP) . | |
| 0 341 493 | 11/1989 | (EP) . | |
| 59-67269 | 4/1984 | (JP) | C07D/215/56 |
| 61-243077 | 10/1986 | (JP) | C07D/401/04 |
| 62-19583 | 1/1987 | (JP) | C07D/401/04 |
| 63-79885 | 4/1988 | (JP) | C07D/401/04 |
| 64-66180 | 3/1989 | (JP) | C07D/401/04 |
| 1-226883 | 9/1989 | (JP) | C07D/401/04 |
| 7-300416 | 11/1995 | (JP) | A61K/31/435 |
| 88/02627 | * | 4/1988 | (WO) . |

OTHER PUBLICATIONS

Domagala et al., J.M., "Quinolone Antibacterials Containing the New 7-[3-(1-Aminoethyl)-pyrrolidinyl] Side Chain: The Effects of the 1-Aminoethyl Moiety and Its Stereochemical Configurations on Potency and in Vivo Efficacy", J. of Medicinal Chemistry, vol. 36, 1993, pp. 871-882.
Marpat 121:108551, abstract of WO 9410163, Demuth, 1994.*
Marpat 121:57343, Kimura, abstract of EP 572259, 1993.*
Marpat 119:28121, Kim, abstract of WO 9303026, 1993.*

* cited by examiner

Primary Examiner—D. Margaret Seaman
(74) Attorney, Agent, or Firm—Sughrue, Mion, Zinn, Macpeak & Seas, PLLC

(57) ABSTRACT

A quinolone derivative represented by formula (I):

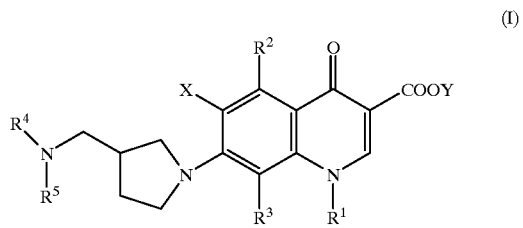

wherein $R^1$ represents a cycloalkyl group; $R^2$ represents a hydrogen atom, an amino group, a hydroxyl group, a thiol group, a halogenomethyl group, an alkyl group, an alkenyl group, an alkynyl group, or an alkoxyl group; $R^3$ represents an amino group, a halogenomethyl group, a halogenomethoxyl group, an alkyl group, an alkenyl group, an alkynyl group, or an alkoxyl group; $R^4$ represents a hydrogen atom or an alkyl group having 1 to 6 carbon atoms; $R^5$ represents a cycloalkyl group having 3 to 6 carbon atoms; the above $R^1$ to $R^5$ may be substituted; X represents a halogen atom or a hydrogen atom; and Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms, or a phenylalkyl group having 1 to 6 carbon atoms in the alkyl moiety thereof, or a salt thereof. The compound exhibits high and broad antimicrobial activity against various bacteria including bacteria resistant to drugs and high safety.

8 Claims, No Drawings

CYCLOALKYLAMINOMETHYLPYRROLIDINE DERIVATIVES

TECHNICAL FIELD

This invention relates to an antimicrobial compound useful as a drug for humans, animals or fishes or an antimicrobial preservative, an antimicrobial agent or preparation containing the same, and a method for treating and/or preventing various infectious diseases using the same.

BACKGROUND ART

Quinolone derivatives having a 3-(cyclopropyl-aminomethyl)pyrrolidinyl group are disclosed in JP-A-59-67269 (the term "JP-A" as used herein means an "unexamined published Japanese patent application"), but a quinolone derivative according to the present invention which has a substituent derived from the cycloalkylaminomethylpyrrolidine compound at the 7-position and a substituent other than a halogen atom at the 8-position and may also have a substituent at the 5-position is unknown.

Recently, many synthetic quinolone antimicrobial agents excellent in not only antimicrobial activity but also in oral absorbability, distribution property to organ, and excretion rate have been developed and provided for clinical use as a chemotherapeutic agent effective on various infectious diseases.

However, low sensitive bacteria resistant to these drugs have recently been increasing in the medicinal field. Further, bacteria resistant to drugs other than quinolone antimicrobial agents have also been acquiring resistance to quinolone antimicrobial agents, as β-lactam resistant *Staphylococcus aureaus* (MRSA). Therefore more effective drugs have been keenly demanded in the field of medicine.

The antimicrobial activity, efficacy and safety of quinolone antimicrobial agents are largely influenced by the substituents at the 7- and 1-positions. And at the same time, the substituents at the 5- and 8-positions also have considerable role to those features. The inventors of the present invention have considered that proper assortment of proper substituents to these positions could provide compounds excellent in antimicrobial activity, efficacy and safety. They have extensively studied seeking a compound exhibiting high antimicrobial activity on a broad range of bacteria including quinolone-resistant bacteria. As a result, it has been found that a quinolone compound having a substituent derived from a cycloalkylaminomethylpyrrolidine compound at the 7-position and having a substituent other than a halogen atom at the 8-position exhibits potent antimicrobial activity toward Gram negative bacteria and Gram positive bacteria, especially Gram positive bacteria including MRSA. It has also been found that the compound additionally having a substituent at the 5-position shows similarly excellent antimicrobial activity.

It has further been found that the compound having a halogenocyclopropyl group, particularly a fluorocyclopropyl group, at the 1-position is excellent in efficacy and safety as well as antimicrobial activity. The present invention has been completed based on these findings.

Of the quinolone derivatives of the present invention having a substituted cyclic alkyl group, e.g., a halogenocyclopropyl group, at the 1-position, a pair of enantiomers attributed only to the halogenocyclopropane ring are present even when there is no stereoisomerism in the substituent at the other position. This is ascribed to the steric relationship between the pyridonecarboxylic acid moiety and the halogen atom on the cyclopropane ring. It is possible to apply a racemic mixture of the enantiomers as a drug as such.

Where stereoisomerism exists at other position in addition to the halogenocyclopropane moiety, particularly at the 7-positioned substituent, such a quinolone derivative embraces diastereomers, that is, at least 4 kinds of stereoisomers are possible. A mixture of diastereomers is a mixture of isomers having different physical properties and is hardly applicable as a drug as such.

The present inventors have made an effort to obtain a quinolone compound as a pure stereoisomer even if there are diastereomers, particularly a pure stereoisomer of 1-(1,2-cis-2-fluorocyclopropyl)-substituted quinolone derivative.

As a result, the present inventors have succeeded in separately obtaining each enantiomer of cis-2-fluorocyclopropylamine as a pure isomer. Starting with this cis-fluorocyclopropylamine, they separately obtained each enantiomer of a quinolone derivative attributed only to the steric configuration of the fluorocyclopropane ring thereof. They also succeeded in obtaining each enantiomer of a cycloalkylaminomethylpyrrolidine compound having an asymmetric carbon atom as a pure isomer.

Now that the above-mentioned quinolone derivative and cycloalkylaminomehylpyrrolidine compound useful as an intermediate have been obtained, it is possible to synthesize an optically active quinolone derivative substantially comprising a pure diastereomer.

DISCLOSURE OF INVENTION

The present invention relates to a compound represented by formula (I):

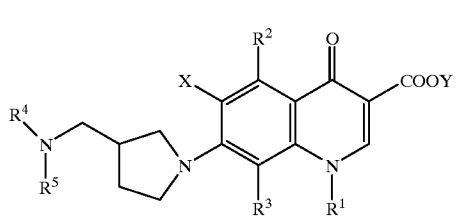

wherein $R^1$ represents a substituted or unsubstituted cyclic alkyl group having 3 to 6 carbon atoms;

$R^2$ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms, or an alkoxyl group having 1 to 6 carbon atoms, and said amino group may have at least one substituent selected from a group of a formyl group, an alkyl group having 1 to 6 carbon atoms and an acyl group having 2 to 5 carbon atoms;

$R^3$ represents an amino group, a halogenomethyl group, a halogenomethoxyl group, an alkyl group having 1 to 6 carbon atoms, an alkenyl group having 2 to 6 carbon atoms, an alkynyl group having 2 to 6 carbon atoms, or an alkoxyl group having 1 to 6 carbon atoms, and said amino group may have at least one substituent selected from a group of a formyl group, an alkyl group having 1 to 6 carbon atoms and an acyl group having 2 to 6 carbon atoms;

$R^4$ represents a hydrogen atom or an alkyl group having 1 to 6 carbon atoms, and said alkyl group may have at least one substituent selected from a group of a hydroxyl group, a halogen atom, an alkylthio group having 1 to 6 carbon atoms and an alkyloxyl group having 1 to 6 carbon atoms;

$R^5$ represents a cyclic alkyl group having 3 to 6 carbon atoms;

X represents a halogen atom or a hydrogen atom; and

Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms, or a phenylalkyl group having 1 to 6 carbon atoms in the alkyl moiety thereof, and a salt thereof.

Further, the present invention relates to the followings:

the compound of formula (I), wherein $R^1$ is a 2-halogenocyclopropyl group, and a salt thereof;

the compound of formula (I), wherein $R^1$ is a 1,2-cis-2-halogenocyclopropyl group, and a salt thereof;

the compound of formula (I), wherein $R^1$ is a substantially stereochemically pure substituent, and a salt thereof;

the compound of formula (I), wherein $R^1$ is a (1R,2S)-2-halogenocyclopropyl group, and a salt thereof;

the compound of formula (I), wherein $R^1$ is a fluorocyclopropyl group, and a salt thereof;

the compound of formula (I), wherein the compound is a substantially stereochemically pure compound, and a salt thereof;

an antimicrobial agent and/or preparation containing the compound of formula (I) or a salt thereof as an active ingredient; and a method for treating and/or preventing an infectious disease by using the compound of formula (I) or a salt thereof.

EMBODIMENTS OF INVENTION

The substituents disclosed in the formula (I) of the present invention are explained below.

The substituent $R^1$ represents a substituted or unsubstituted cyclic alkyl group having 3 to 6 carbon atoms. The cyclic alkyl group is preferably a cyclopropyl group. The substituent of the substituted cyclic alkyl group is preferably a halogen atom, particularly a fluorine atom. Where $R^1$ is a halogenocyclopropyl group, the halogen atom and the pyridonecarboxylic acid moiety are preferably in a cis-configuration with respect to the cyclopropane ring.

The substituent $R^2$ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms, or an alkoxyl group having 1 to 6 carbon atoms, and said amino group may have at least one substituent selected from a group of a formyl group, an alkyl group having 1 to 6 carbon atoms and an acyl group having 2 to 5 carbon atoms.

The alkyl group as $R^2$ can be straight or branched of from 1 to 6 carbon atoms and preferably includes a methyl group, an ethyl group, an n-propyl group, and an isopropyl group. The alkenyl group as $R^2$ can be straight or branched of from 2 to 6 carbon atoms and is preferably a vinyl group. The alkynyl group as $R^2$ can be straight or branched of from 2 to 6 carbon atoms and is preferably an ethynyl group. The halogen atom of halogenomethyl group as $R^2$ is preferably a fluorine atom and the number of the halogen atom is from 1 to 3. The alkoxyl group as $R^2$ can be of from 1 to 6 carbon atoms and is preferably a methoxyl group.

The substituent $R^3$ represents an amino group, a halogenomethyl group, a halogenomethoxyl group, an alkyl group having 1 to 6 carbon atoms, an alkenyl group having 2 to 6 carbon atoms, an alkynyl group having 2 to 6 carbon atoms, or an alkoxyl group having 1 to 6 carbon atoms, and said amino group may have at least one substituent selected from a group of a formyl group, an alkyl group having 1 to 6 carbon atoms and an acyl group having 2 to 6 carbon atoms.

The alkyl group as $R^3$ can be straight or branched of from 1 to 6 carbon atoms and is preferably a methyl group or an ethyl group. The alkenyl group as $R^3$ can be straight or branched of from 2 to 6 carbon atoms and is preferably a vinyl group. The alkynyl group as $R^3$ can be straight or branched of from 2 to 6 carbon atoms and is preferably an ethynyl group. The halogen atom of halogenomethyl group as $R^3$ is preferably a fluorine atom and the number of the halogen atom is from 1 to 3. The alkoxyl group as $R^3$ is preferably a methoxyl group. The halogen atom of halogenomethoxyl group as $R^3$ is preferably a fluorine atom and the number of the halogen atom is from 1 to 3.

The substituent $R^4$ represents a hydrogen atom or an alkyl group having 1 to 6 carbon atoms, and said alkyl group may have at least one substituent selected from a group of a hydroxyl group, a halogen atom, an alkylthio group having 1 to 6 carbon atoms and an alkyloxy group having 1 to 6 carbon atoms.

The alkyl group as $R^4$ can be straight or branched of from 1 to 6 carbon atoms and preferably includes a methyl group, an ethyl group, an n-propyl group, and an isopropyl group. The hydroxyl-substituted alkyl group as $R^4$ can be straight or branched of from 1 to 6 carbon atoms and is preferably a hydroxyethyl group or a hydroxypropyl group.

The substituent $R^5$ represents a cyclic alkyl group having 3 to 6 carbon atoms, preferably a cyclopropyl group or a cyclobutyl group.

The substituent X represents a halogen atom or a hydrogen atom. The halogen atom as X is preferably a fluorine atom.

The substituent Y represents a hydrogen atom, a phenyl group, an acetoxymethyl group, a pivaloyloxymethyl group, an ethoxycarbonyl group, a choline group, a dimethylaminoethyl group, a 5-indanyl group, a phth[]alidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms, or a phenylalkyl group having 1 to 6 carbon atoms in the alkyl moiety thereof.

Where $R^2$ or $R^3$ is an amino group, a hydroxyl group or a thiol group, it may be protected with a protective group used in this field.

Examples of such protective groups include an alkoxycarbonyl group, e.g., a t-butoxycarbonyl group, a 2,2,2-trichloroethoxycarbonyl group; an aralkyloxycarbonyl group, e.g., a benzyloxycarbonyl group, a p-methoxybenzyloxycarbonyl group, and a p-nitrobenzyloxycarbonyl group; an acyl group, e.g., an acetyl group, a methoxyacetyl group, a trifluoroacetyl group, a chloroacetyl group, a pivaloyl group, a formyyl group, and a benzoyl group; an alkyl or aralkyl group, e.g., a t-butyl group, a benzyl group, a p-nitrobenzyl group, a p-methoxybenzyl group, and a triphenylmethyl group; an ether group, e.g., a methoxymethyl group, a t-butoxymethyl group, a tetrahydropyranyl group, and a 2,2,2-trichloroethoxymethyl group; and a silyl group, e.g., a trimethylsilyl group, an isopropyldimethylsilyl group, a t-butyldimethylsilyl group, a tribenzylsilyl group, and a t-butyldiphenylsilyl group. The compound of the invention having such protected substituents are particularly useful as an intermediate.

A preferable assortment of $R^2$ and $R^3$ in the compound of formula (I) is as follows: $R^2$ is an amino group, a hydrogen atom, a hydroxyl group or an alkyl group having 1 to 6 carbon atoms while $R^3$ is an alkyl group having 1 to 6 carbon atoms, an alkoxyl group having 1 to 6 carbon atoms or a halogenomethoxyl group.

It is still preferred that $R^2$ is an amino group, a hydrogen atom, a hydroxyl group or a methyl group while $R^3$ is a methyl group, a methoxyl group or a difluoromethoxyl group.

Where $R^2$ and $R^3$ are selected from the above assortments, X is preferably a fluorine atom.

The compound of formula (I) in which $R^1$ is a halogenocyclopropyl group will be described in detail.

The halogen atom on the cyclopropyl group includes a fluorine atom and a chlorine atom, with a fluorine atom being particularly preferred. The halogen atom and the pyridonecarboxylic acid moiety are preferably in a cis-configuration with respect to the cyclopropane ring. Regardless of stereoisomerism of the 7-positioned substituent, the 1-positioned cis-2-halogenocyclopropyl moiety makes a pair of enantiomers, each of which was observed to exhibit potent antimicrobial activity and high safety.

Where the compound of formula (I) has such a structure that contains diastereomers, it is preferable to administer to humans or animals a compound substantially comprising a pure diastereomer. The term "a compound substantially comprising a pure diastereomer" as used herein is construed as including not only a compound containing no other diastereomer but a compound containing other diastereomers to such an extent that the compound is recognized to be stereochemically pure as a whole. In other words, it is construed as meaning that other diastereomers may exist to some extent as long as the existence gives no substantial influence on physiological activities or physicochemical constants.

The term "substantially stereochemically pure" as used herein is intended to mean that a compound substantially comprising a single steric isomer of the compound ascribed to its asymmetric carbon atom. The latitude of the term "pure" in "pure diastereomer" also applies here.

The pyridonecarboxylic acid derivative of the present invention may have either a free form or a form of an acid addition salt or a carboxylic acid salt. Acid addition salts include inorganic acid salts, such as hydrochlorides, sulfates, nitrates, hydrobromides, hydroiodides, and phosphates; and organic acid salts, such as acetates, methanesulfonates, benzenesulfonates, toluenesulfonates, citrates, maleates, fumarates, and lactates.

The carboxylic acid salts include both inorganic salts and organic salts, such as alkali metal salts, e.g., lithium salts, sodium salts, and potassium salts; alkaline earth metal salts, e.g., magnesium salts and calcium salts; ammonium salts; triethylamine salts, N-methylglucamine salts, and tris-(hydroxymethyl)aminomethane salts.

The free pyridonecarboxylic acid derivatives, acid addition salts thereof, and carboxylic acid salts thereof may be present as a hydrate.

On the other hand, quinolone derivatives with the carboxylic acid moiety thereof having an ester form are useful as a synthetic intermediate or a pro-drug (a drug precursor). For example, alkyl esters, benzyl esters, alkoxyalkyl esters, phenylalkyl esters, and phenyl esters are useful as synthetic intermediates.

Esters which can be used as pro-drugs are esters which are easily cleaved in vivo to produce a free carboxylic acid, including acetoxymethyl esters, pivaloyloxymethyl esters, ethoxycarbonyl esters, choline esters, dimethylaminoethyl esters, 5-indanyl esters, phthalidinyl esters, 5-alkyl-2-oxo-1,3-dioxol-4-ylmethyl esters, and oxoalkyl esters, such as 3-acetoxy-2-oxobutyl esters.

The compound of formula (I) can be prepared through various processes. A preferred process comprises reacting a compound represented by formula (II):

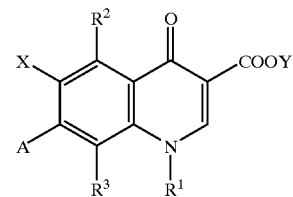

(II)

wherein $R^1$, $R^2$, $R^3$, and X are as defined above; A represents a substituent serves as a leaving group, such as a fluorine atom, a chlorine atom, a bromine atom, an alkylsulfonyl group having 1 to 3 carbon atoms or an arylsulfonyl group (e.g., a benzenesulfonyl group or a toluenesulfonyl group); and Y has the same meaning as Y in formula (I) and additionally represents a substituent of formula (III):

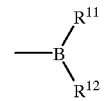

(III)

wherein $R^{11}$ and $R^{12}$ each represent a fluorine atom or a lower alkylcarbonyloxy group, with a compound represented by formula (IV):

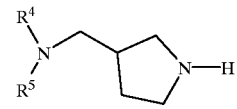

(IV)

wherein $R^4$ has the same meaning as $R^4$ in formula (I) and additionally represents a nitrogen protective group Rx; and $R^5$ is as defined above, or an acid addition salt thereof.

The nitrogen protective group Rx are those ordinary used in this field. Examples of Rx are; an alkyloxycarbonyl group, e.g., a t-butoxycarbonyl group and a 2,2,2-trichloroethoxycarbonyl group; an aralkyloxycarbonyl group, e.g., a benzyloxycarbonyl group, a paramethoxybenzyloxycarbonyl group, and a paranitrobenzyloxycarbonyl group; an acyl group, e.g., an acetyl group, a methoxyacetyl group, a trifluoroacetyl group, a chloroacetyl group, a pivaloyl group, a formyl group, and a benzoyl group; an alkyl group or an aralkyl group, e.g., a t-butyl group, a benzyl group, a paranitrobenzyl group, a paramethoxybenzyl group, and a triphenylmethyl group; an ether group, e.g., a methoxymethyl group, a t-butoxymethyl group, a tetrahydropyranyl group, and a 2,2,2-trichloroethoxymethyl group; and a silyl group, e.g., a trimethylsilyl group, an isopropyldimethylsilyl group, a t-butyldimethylsilyl group, a tribenzylsilyl group, and a t-butyldiphenylsilyl group.

The resulting compound in which Y is an alkyl group having 1 to 6 carbon atoms, an alkoxymethyl group having 2 to 7 carbon atoms or a phenylalkyl group having 1 to 6 carbon atoms in the alkyl moiety thereof can be converted to the corresponding carboxylic acid by hydrolysis under an acidic or basic condition commonly used for hydrolysis of carboxylic esters. The protective group, if any, is removed under properly selected conditions to obtain a desired compound (I).

The compound obtained by the substitution reaction between the compound (II) wherein Y is the group (III) and the compound (IV) can be converted to the corresponding carboxylic acid by treatment with an acidic or basic compound.

The substitution reaction between the compounds (II) and (IV) is carried out with or without a solvent. The solvent, if used, is not limited as long as it is inert under the reaction conditions. Suitable solvents include dimethyl sulfoxide, pyridine, acetonitrile, ethanol, chloroform, dimethylformamide, dimethylacetamide, N-methylpyrrolidone, tetrahydrofuran, water, and 3-methoxybutanol. These solvents may be used as a mixture thereof.

The reaction is usually performed within the range of room temperature to 200° C., preferably 25 to 150° C., for 0.5 to 48 hours. The reaction usually completes in about 0.5 to 2 hours. It is advantageous to conduct the reaction in the presence of an acid acceptor, such as an inorganic base (e.g., an alkali metal or alkaline metal carbonate or hydrogencarbonate) or an organic base (e.g., triethylamine or pyridine).

The optically active cis-2-fluorocyclopropylamine, which substantially comprises a-pure isomer and is preferred as a starting compound for the synthesis of the compound (I) substantially comprising a pure isomer, can be synthesized by, for example, the process described in JP-A-2-231475. The thus obtained cis-2-fluorocyclopropylamine derivative is led to the compound of formula (II) substantially comprising a pure isomer by, for example, the process described in JP-A-2-231475.

The compounds of the present invention have potent antimicrobial activity and are therefore useful as drugs for humans, animals or fishes, agricultural chemicals, or food preservatives.

For use as drugs for humans, the dose of the compound is in the range of from 50 mg to 1 g, and preferably from 100 mg to 300 mg, per day for adults.

For veterinary use, the dose is generally in the range of from 1 to 200 mg, and preferably from 5 to 100 mg, per kg of body weight per day while varying depending on the purpose of administration (e.g., for therapy or for prevention), etc., the kind and the size of the animal, the kind of the pathogenic organisms, and severity of symptom.

The above-mentioned daily dose is given once a day or in 2 to 4 divided doses. If necessary, a daily dose may exceed the above-specified range.

The compounds according to the present invention are active on a broad range of microorganisms causing various infectious diseases and effective to prevent, alleviate or cure diseases caused by these pathogens. Examples of bacteria or bacterium-like microorganisms on which the compounds of the invention are effective include Staphylococci, *Streptococcus pyogenes, Streptococcus haemolyticus, Streptococcus fecalis, Streptococcus pneumoniae*, Peptostreptococci, *Neisseria gonorrhoeae, Escherichia coli*, Citrobacter sp., Shigella sp., *Klebsiella pneumoniae*, Enterobacter sp., Serratia sp., Proteus sp., *Pseudomonas aeruginosa, Haemophilus influenzae*, Acinetobacter sp., Campylobacter sp., and *Chlamydozoon trachomatis*.

Diseases which are caused by these pathogens include folliculitis, furuncle, carbuncle, erysipelas, phlegmon, lymphangitis/lymphadenitis, felon, subcutaneous abscess, spiradenitis, acne agminata, infectious atheroma, perianal abscess, mastadenitis, superficial secondary infections after trauma, burn or surgery trauma, pharyngolaryngitis, acute bronchitis, tonsillitis, chronic bronchitis, bronchiectasis, diffuse panbronchiolitis, secondary infections of chronic respiratory diseases, pneumonia, pyelonephritis, cystitis, prostatitis, epididymitis, gonococcal urethritis, non-gonococcal urethritis, cholecystitis, cholangitis, bacillary dysentery, enteritis, adnexitis, intrauterine infections, bartholinitis, blepharitis, hordeolum, dacryocystitis, tarsadenitis, keratohelcosis, otitis media, sinusitis, paradentosis, pericoronitis, gnathitis, peritonitis, endocarditis, septicemia, meningitis, and skin infections.

The compounds of the present invention are also effective on various microorganisms causing veterinary diseases, such as those belonging to the genera Escherichia, Salmonella, Pasteurella, Haemophilus, Bordetella, Staphylococcus, and Mycoplasma. Illustrative examples of the veterinary diseases include those of fowl, such as colibacillosis, pullorum disease, avian paratyphosis, fowl cholera, infectious coryza, staphylomycosis, and mycoplasmosis; those of pigs, such as colibacillosis, salmonellosis, pasteurellosis, hemophilus infections, atrophic rhinitis, exudative epidermitis, and mycoplasmosis; those of cattle, such as colibacillosis, salmonellosis, hemorrhagic septicemia, mycoplasmosis, bovine contagious pleuropneumonia, and bovine mastitis; those of dogs, such as colisepsis, salmonellosis, hemorrhagic septicemia, pyometra, and cystitis; those of cats, such as exudative pleurisy, cystitis, chronic rhinitis, and hemophilus infections; and those of kittens, such as bacterial diarrhea and mycoplasmosis.

Dosage forms of pharmaceutical preparations containing the compound of the present invention are appropriately selected according to the administration route and can be prepared by conventional preparation methods. Examples of dosage forms for oral administration include tablets, powders, granules, capsules, solutions, syrups, elixirs, and oily or aqueous suspensions.

Injectable preparations may contain adjuvants, such as stabilizers, antiseptics, and solubilizers. The injectable solution which may contain these adjuvants may be put into a container and solidified by, for example, lyophilization to prepare a solid preparation which is dissolved on use. The container may contain either a single dose or multiple doses.

Preparations for external application include solutions, suspensions, emulsions, ointments, gels, creams, lotions, and sprays.

Solid preparations may contain, in addition to the active compound, pharmaceutically acceptable additives. For example, the active compound is mixed with additives selected according to necessity from among fillers, extenders, binders, disintegrators, absorption accelerators, wetting agents, and lubricants and formulated into solid preparations.

Liquid preparations include solutions, suspensions, and emulsions. They may contain adjuvants, such as suspending agents, emulsifiers, and so forth.

The compound can be administered to animals orally either directly or by mixing with feedstuff, or in a dissolved form directly given to animals or by mixing with water or feedstuff or non-orally by injection.

For veterinary use, the compound can be formulated into powders, fine granules, soluble powders, syrups, solutions, and injections according to the customary methods in the art.

The present invention will now be illustrated by way of Formulation Examples, Reference Examples, and Examples, but the present invention should not be construed as being limited thereto. All the percents are by weight unless otherwise indicated.

Formulation Example 1

| Capsules | |
| --- | --- |
| Compound of Example 2 | 100.0 mg |
| Corn starch | 23.0 mg |
| CMC·Ca | 22.5 mg |
| Hydroxymethyl cellulose | 3.0 mg |
| Magnesium stearate | 1.5 mg |
| Total | 150.0 mg |

Formulation Example 2

| Solution | |
| --- | --- |
| Compound of Example 2 | 1 to 10 g |
| Acetic acid or sodium hydroxide | 0.5 to 2 g |
| Ethyl p-hydroxybenzoate | 0.1 g |
| Purified water | 87.9 to 98.4 g |
| Total | 100 g |

Formulation Example 3

| Powder for Mixing with Feed | |
| --- | --- |
| Compound of Example 2 | 1 to 10 g |
| Corn starch | 89.5 to 98.5 g |
| Light anhydrous silicic acid | 0.5 g |
| Total | 100 g |

BEST MODE FOR CARRYING OUT INVENTION

EXAMPLES

Reference Example 1
(3R)-N-Cyclopropyl-1-[(R)-phenylethyl]-5-oxopyrrolidine-3-carboxamide To a solution of 2.33 g (10 mmol) of (3R)-1-[(R)-phenylethyl]-5-oxopyrrolidine-3-carboxylic acid in 20 ml of acetonitrile was added 1.83 g (11.5 mol) of 1,1'-carbonyldiimidazole, and the mixture was heated at 60° C. for 1 hour. The reaction mixture was cooled, and 655 mg (11.5 mmol) of cyclopropylamine was added thereto while cooling with ice, followed by stirring at room temperature for 19 hours. The solvent was evaporated, and chloroform was added to the residue. The mixture was washed successively with a 10% citric acid aqueous solution and water, and dried over sodium sulfate. The solvent was evaporated to give 2.56 g (94%) of the title compound.

$^1$H-NMR (CDCl$_3$) δ ppm: 0.45–0.51 (2H, m), 0.70–0.80 (2H, m), 1.53 (3H, d, J=6.84 Hz), 2.53–2.59 (1H, m), 2.67–2.83 (3H, m), 3.07–3.12 (1H, m), 3.53–3.67 (1H, m), 5.44–5.49 (1H, m), 5.82 (1H, brs), 7.25–7.35 (5H, m).

Reference Example 2
(3R)-3-(N-Cyclopropylaminomethyl)-1-[(R)-phenylethyl]pyrrolidine To a solution of 2 g (7.35 mol) of (3R)-N-cyclopropyl-1-[(R)-phenylethyl]-5-oxopyrrolidine-3-carboxamide in 60 ml of tetrahydrofuran was added a 37 ml of a solution containing 1 mmol of a borane-tetrahydrofuran complex under ice-cooling, and the mixture was stirred at room temperature for 17 hours. The solvent was evaporated, and chloroform was added to the residue. The mixture was washed with a saturated sodium chloride aqueous solution and dried over sodium sulfate. The solvent was evaporated, and a 5N sodium hydroxide aqueous solution was added to the residue, followed by refluxing for 5 hours. After cooling, a saturated sodium chloride aqueous solution was added to the reaction mixture, and the mixture was extracted with chloroform. The extract was dried over sodium sulfate, and the solvent was evaporated to give 1.63 g (91%) of the title compound.

$^1$H-NMR (CDCl$_3$) δ ppm: 0.27–0.31 (2H, m), 0.38–0.43 (2H, m), 1.36–1.47 (1H, m), 1.37 (3H, d, J=6.83 Hz), 1.89–1.98 (1H, m), 2.04–2.11 (2H, m), 2.27–2.59 (3H, m), 2.65 (2H, d, J=7.32 Hz), 2.81–2.88 (1H, m), 3.14–3.19 (1H, m), 7.20–7.34 (5H, m).

Reference Example 3
(3R)-3-(N-t-Butoxycarbonyl-N-cyclopropyl-aminomethyl)-1-[(R)-phenylethyl]pyrrolidine To a solution of 1.63 g (6.68 mmol) of (3R)-3-(N-cyclopropylaminomethyl)-1-[(R)-phenylethyl]pyrrolidine in 30 ml of dichloromethane were added 1.75 g (8 mol) of di-t-butyl dicarbonate, 8 ml of triethylamine, and 10 mg of 4-dimethylaminopyridine, followed by stirring at room temperature for 20 minutes. The solvent was evaporated, and the residue was purified by silica gel column chromatography to give 2.2 g (96%) of the title compound from a 3% methanolchloroform eluate.

$^1$H-NMR (CDCl$_3$) δ ppm: 0.53–0.58 (2H, m), 0.70–0.74 (2H, m), 1.37 (3H, d, J=6.35 Hz), 1.44 (9H, s), 1.85–1.94 (1H, m), 2.13–2.18 (1H, m), 2.41–2.64 (4H, m), 2.78–2.82 (1H, m), 3.14–3.25 (4H, m), 7.22–7.33 (5H, m).

Reference Example 4
(3R)-3-(N-t-Butoxycarbonyl-N-cyclopropylaminomethyl)pyrrolidine To a solution of 1.7 g (4.9 mmol) of (3R)-N-t-butoxycarbonyl-N-cyclopropylaminomethyl-1-[(1R)-phenylethyl]pyrrolidine in 50 ml of ethanol was added 1.7 g of 10% palladium-on-carbon. Catalytic hydrogenation was conducted under a 4 atom of hydrogen atmosphere, while the reaction vessel was heated by an irradiation with a tungsten lamp. The catalyst was removed by filtration, and the solvent was removed from the filtrate by evaporation to give 1.2 g (100%) of the title compound.

$^1$H-NMR (CDCl$_3$) δ ppm: 0.60 (2H, brs), 0.75–0.85 (2H, m), 1.96 (9H, s), 1.72–1.85 (1H, m), 2.10–2.20 (1H, m), 2.45–2.54 (1H, m), 2.65–2.79 (1H, m), 2.94–3.03 (1H, m), 3.21–3.51 (5H, m).

Example 1
7-[3-(R)-Cyclopropylaminomethyl-1-pyrrolidinyl]-6-fluoro-1-[(1R,2S)-2-fluorocyclopropyl]-1,4-dihydro-8-methyl-4-oxoquinoline-3-carboxylic Acid To a solution of 690 mg (2 mmol) of 6,7-difluoro-1-[(1R,2S)-2-fluorocyclopropyl]-1,4-dihydro-8-methyl-4-oxoquinoline-3-carboxylic acid $BF_2$ chelate in 8 ml of dimethyl sulfoxide were added 960 mg (4 mmol) of (3R)-3-(N-t-butoxycarbonyl-N-cyclopropylaminomethyl) pyrrolidine and 1 ml of triethylamine, and the mixture was stirred at room temperature for 170 hours. Triethylamine was removed by evaporation, and 10 ml of water was added to the residue, followed by stirring at room temperature for 15 minutes. The precipitated crystals were washed with water and collected by filtration. The crystals were dissolved in 100 ml of a 4:1 mixture of ethanol and water, and 10 ml of triethylamine was added thereto, followed by refluxing for 3 hours. The solvent was evaporated, and 100 ml of chloroform was added to the residue. The mixture was washed with two 30 ml portions of 10% citric acid aqueous solution, and dried over magnesium sulfate. The solvent was evaporated, and 10 ml of concentrated hydrochloric acid was added to the residue. The mixture was stirred at room temperature for 5 minutes, washed with two 10 ml portions of chloroform, adjusted to a pH of 7.3 with a 20% sodium hydroxide aqueous solution, and extracted with three 80 ml portions of chloroform. The extract was dried over sodium sulfate, and the solvent was evaporated. The residue was purified by preparative thin layer chromatography (TLC) (developed with the lower layer of a mixture of chloroform:methanol:water=7:3:1) to give 181 mg (22%) of a crude product. Recrystallization from ethanoldiethyl ether gave 100 mg of the title compound.

$^1$H-NMR (0.1N-NaOD) δ ppm: 0.30–0.36 (2H, m), 0.41–0.50 (2H, m), 1.04–1.20 (1H, m), 1.42–1.65 (2H, m), 2.00–2.17 (2H, m), 2.28–2.46 (1H, m), 2.36 (3H, s), 2.63–2.75 (2H, m), 3.19–3.35 (3H, m), 3.54–3.68 (1H, m), 3.96–4.04 (1H, m), 4.99–5.07 (0.5H, m), 7.61 (1H, d, J=14.16 Hz), 8.42 (1H, s).

Elementary analysis for $C_{22}H_{25}F_2N_3O_3 \cdot 0.25H_2O$: Calcd. (%): C 62.62; H 6.09; N 9.69; Found (%): C 62.87; H 6.11; N 9.83; Melting point: 163–164° C.

Example 2

5-Amino-7-[3-(R)-(N-cyclopropylaminomethyl)-1-pyrrolidinyl]-6-fluoro-1-[(1R,2S)-2-fluorocyclopropyl]-1,4-dihydro-8-methoxy-4-oxocquinoline-3-carboxylic Acid To a solution of 328 mg (1 mmol) of 5-amino-6,7-difluoro-1-[(2S)-fluoro-(1R)-cyclopropyl]-1,4-dihydro-8-methoxy-4-oxoquinoline-3-carboxylic acid in 10 ml of dimethyl sulfoxide were added 360 mg (1.5 mmol) of (3R)-3-(N-t-butoxycarbonyl-N-cyclopropylaminomethyl) pyrrolidine and 3 ml of triethylamine, and the mixture was heated at 100° C. for 15 hours. The solvent was evaporated, and 50 ml of chloroform was added to the residue. The chloroform solution was washed with two 20 ml portions of a 10% citric acid aqueous solution and dried over sodium sulfate, and the solvent was evaporated. To the residue was added 5 ml of concentrated hydrochloric acid, followed by stirring at room temperature for 5 minutes. The reaction mixture was washed with two 20 ml portions of chloroform. The hydrochloric acid solution was adjusted to a pH of 7.3 with a 20% sodium hydroxide aqueous solution and extracted with three 80 ml portions of chloroform. The extract was dried over sodium sulfate, and the solvent was evaporated. The residue was purified by preparative TLC (developed with the lower layer of a mixture of chloroform:methanol:water=7:3:1) to obtain a crude compound. Recrystallization from diethyl ether yielded 215 mg (48%) of the title compound.

$^1$H-NMR (0.1N-NaOD) δ ppm: 0.33 (2H, brs), 0.46–0.48 (2H, m), 1.17–1.27 (1H, m), 1.34–1.47 (1H, m), 1.57–1.59 (1H, m), 2.08–2.14 (2H, m), 2.39–2.43 (1H, m), 2.72 (2H, brs), 3.34–3.35 (1H, m), 3.43 (3H, 2s), 3.56–3.65 (2H, m), 3.86–3.89 (1H, m), 5.02 (0.5H, brs), 8.21 (1H, 2s).

Elementary analysis for $C_{19}H_{20}F_2N_4O_4 \cdot 0.25H_2O$: Calcd. (%): 58.48; H 5.86; N 11.97; Found (%): 53.34; H 5.90; N 12.37; Melting point: 154–156° C. (with decomposition)

Example 3

5-Amino-7-[(3R)-N-cyclopropylaminomethyl-1-pyrrolidinyl]-6-fluoro-1-[(1R,2S)-2-fluorocyclopropyl]-1,4-dihydro-8-methyl-4-oxoquinoline-3-carboxylic Acid Hydrochloride To a solution of 2.00 g (6.4 mmol) of 5-amino-6,7-difluoro-1-[(2S)-fluoro-(1R)-cyclopropyl]-1,4-dihydro-8-methyl-4-oxoquinoline-3-carboxylic acid in 10 ml of dimethyl sulfoxide were added 2.32 g (9.6 mmol) of (3R)-N-t-butoxycarbonyl-N-cyclopropylaminomethylpyrrolidine and 30 ml of triethylamine, and the mixture was heated at 120° C. for 5 days. The solvent was evaporated, and to the residue was added 10 ml of concentrated hydrochloric acid, followed by stirring at room temperature for 15 minutes. The reaction mixture was washed with two 300 ml portions of chloroform. The hydrochloric acid solution was adjusted to a pH of 7.3 with a 20% sodium hydroxide aqueous solution and extracted with three 200 ml portions of chloroform. The extract was dried over sodium sulfate, and the solvent was evaporated. The residue was purified by preparative TLC (developed with the lower layer of a mixture of chloroform:methanol:water=7:3:1), 10 ml of 1N hydrochloric acid was added to the crude product, and the solvent was evaporated. Recrystallization from ethanol-diethyl ether yielded 1.05 g (31%) of the title compound.

$^1$H-NMR (0.1N NaOD-$D_2O$) δ ppm: 0.34 (1H, brs), 0.47 (1H, brs), 1.03–1.16 (1H, m), 1.42–1.61 (2H, m), 2.04–2.80 (6H, m), 3.25–3.42 (3H, m), 3.66–3.74 (1H, m), 3.88–3.97 (1H, m), 8.26 (1H, s)

Elementary analysis for $C_{23}H_{29}F_2N_4O_3 \cdot HCl \cdot 2.5H_2O \cdot 0.25EtOH$: Calcd. (%): C 51.82; H 6.47; N 10.74; Found (%): C 51.94; H 5.91; N 10.20; Melting point: 145–149° C.

The antimicrobial activity of the compounds obtained in Examples 1 to 3 was examined in accordance with the standard method specified by the Japan Chemotherapeutic Society. The resulting antimicrobial spectra are shown in Table 1 below.

TABLE 1

| Antimicrobial Spectra (MIC: μg/ml) | | | |
|---|---|---|---|
| Test Microorganism | Example 1 | Example 2 | Example 3 |
| E. coli, NIHJ | ≦0.003 | 0.006 | 0.006 |
| S. flexneli, 2A 5503 | 0.006 | 0.013 | 0.006 |
| Pr. vulgaris, 08601 | 0.006 | 0.10 | 0.05 |
| Pr. mirabilis, IFO-3849 | 0.025 | 0.20 | 0.10 |
| Ser. marcescens, 10100 | 0.10 | 0.39 | 0.20 |
| Ps. aeruginosa, 32104 | 0.20 | 0.78 | 0.39 |
| Ps. aeruginosa, 32121 | 0.10 | 0.78 | 0.20 |
| Ps. maltophilia, IID-1275 | 0.05 | 0.20 | 0.10 |
| S. aureus, 209P | ≦0.003 | ≦0.003 | ≦0.003 |
| S. epidermidis, 56500 | 0.013 | 0.013 | 0.006 |
| Str. pyrogenes, G-36 | 0.013 | 0.025 | 0.013 |
| Str. faecalis, ATCC-19433 | 0.025 | 0.10 | 0.05 |
| S. aureaus, 870307 | 0.025 | 0.05 | 0.025 |

What is claimed is:

1. A compound represented by the formula (I) or a salt thereof:

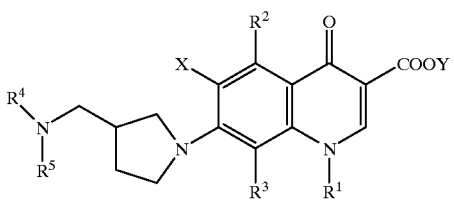

(I)

wherein

- $R^1$ represents a substituted cyclic alkyl group having 3 to 6 carbon atoms;
- $R^2$ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms, or an alkoxyl group having 1 to 6 carbon atoms, and wherein said amino group may have at least one substituent selected from the group consisting of a formyl group, an alkyl group having 1 to 6 carbon atoms and an acyl group having 2 to 5 carbon atoms;
- $R^3$ represents an amino group, a halogenomethyl group, a halogenomethoxyl group, an alkenyl group having 2 to 6 carbon atoms, or an alkynyl group having 2 to 6 carbon atoms, and wherein said amino group may have at least one substituent selected from the group consisting of a formyl group, an alkyl group having 1 to 6 carbon atoms and an acyl group having 2 to 6 carbon atoms;
- $R^4$ represents a hydrogen atom or an alkyl group having 1 to 6 carbon atoms, and wherein said alkyl group may have at least one substituent selected from the group consisting of a hydroxyl group, a halogen atom, an alkylthio group having 1 to 6 carbon atoms and an alkyloxyl group having 1 to 6 carbon atoms;
- $R^5$ represents a cyclic alkyl group having 3 to 6 carbon atoms;
- X represents a halogen atom or a hydrogen atom; and
- Y represents a hydrogen atom, a phenyl group, an acetoxymethyl group, a pivaloyloxymethyl group, an ethoxymethyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms, or a phenylalkyl group having 1 to 6 carbon atoms in the alkyl moiety thereof.

2. The compound according to claim 1, wherein $R^1$ is a 2-halogenocyclopropyl group or a salt thereof.

3. The compound according to claim 1, wherein $R^1$ is a 1,2-cis-2-halogenocyclopropyl group or a salt thereof.

4. The compound according to any one of claims 1 to 3, wherein $R^1$ is a substantially stereochemically pure substituent or a salt thereof.

5. The compound according to claim 4, wherein $R^1$ is a (1R,2S)-2-halogenocyclopropyl group or a salt thereof.

6. The compound according to claim 2, 3, or 5, wherein $R^1$ is a fluorocyclopropyl group or a salt thereof.

7. The compound according to claim 6, wherein the compound is a substantially stereochemically pure compound or a salt thereof.

8. An antimicrobial composition comprising as an active ingredient, a compound according to claim 1 or a salt thereof, and a pharmaceutically acceptable carrier.

* * * * *